(12) United States Patent
Yoo et al.

(10) Patent No.: US 8,653,256 B2
(45) Date of Patent: Feb. 18, 2014

(54) METHOD OF PRODUCING TURANOSE USING AMYLOSUCRASE, AND SWEETENER USING THE TURANOSE

(75) Inventors: Sang-Ho Yoo, Seoul (KR); Ren Wang, Seoul (KR); Cheon-Seok Park, Seongnam-si (KR)

(73) Assignee: Industry-Academia Cooperation Group of Sejong University, Seoul (KR)

( * ) Notice: Subject to any disclaimer, the term of this patent is extended or adjusted under 35 U.S.C. 154(b) by 0 days.

(21) Appl. No.: 13/497,609

(22) PCT Filed: Jan. 31, 2011

(86) PCT No.: PCT/KR2011/000645
§ 371 (c)(1),
(2), (4) Date: Mar. 22, 2012

(87) PCT Pub. No.: WO2012/060519
PCT Pub. Date: May 10, 2012

(65) Prior Publication Data
US 2012/0238744 A1    Sep. 20, 2012

(30) Foreign Application Priority Data

Nov. 2, 2010  (KR) .......................... 10-2010-0108174

(51) Int. Cl.
*C12P 19/18*    (2006.01)
(52) U.S. Cl.
USPC .................................................... 536/123.13
(58) Field of Classification Search
USPC ................................................... 536/123.13
See application file for complete search history.

(56) References Cited

U.S. PATENT DOCUMENTS

| | | |
|---|---|---|
| 6,265,635 B1 | 7/2001 | Kossmann et al. |
| 6,818,421 B2 | 11/2004 | Kossmann et al. |
| 7,456,003 B2 | 11/2008 | Kossmann et al. |

FOREIGN PATENT DOCUMENTS

| | | |
|---|---|---|
| JP | 3182665 B2 | 4/2001 |
| KR | 10-0352532 B1 | 2/2004 |
| KR | 10-2009-0081491 A | 7/2009 |

OTHER PUBLICATIONS

Albenne et al. Molecular Basis of the Amylose-like Polymer Formation Catalyzed by Neisseria polysaccharea Amylosucrase. 279:726-734, 2004.*
Gabrielle Potocki De Montalk et al., "Amylosucrase from Neisseria polysaccharea: novel catalytic properties", FEBS Letters, 2000, pp. 219-223, vol. 471.
Shigeyuki Hamada, "Role of sweeteners in the etiology and prevention of dental caries", Pure Appl. Chem., 2002, pp. 1293-1300, vol. 74, No. 7.
Mary An Godshall, "The Expanding World of Nutritive and Non-Nutritive Sweeteners", Sugar Journal, Jan. 2007, pp. 12-20.

* cited by examiner

*Primary Examiner* — Wu-Cheng Winston Shen
*Assistant Examiner* — Yi-Horng Shiao
(74) *Attorney, Agent, or Firm* — Sherr & Jiang, PLLC

(57) ABSTRACT

The present invention relates a method of producing turanose using amylosucrase and a sweetener including the turanose. This method enables production of high-purity turanose through an enzymatic reaction occurring by treating a solution including only sucrose or a solution including fructose and sucrose with amylosucrase.

6 Claims, 3 Drawing Sheets

SEQUENCE LISTING

```
<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: NPAS1

<400> SEQUENCE: 1
ggatccgatg ttgaccccca cgcagcaa                                    28

<210> SEQ ID NO 2
<211> LENGTH: 29
<212> TYPE: DNA
<213> ORGANISM: Artificial Sequence
<220> FEATURE:
<223> OTHER INFORMATION: NPAS2

<400> SEQUENCE: 2
ggcaagcttc aggcgatttc gagccacat                                   29
```

METHOD OF PRODUCING TURANOSE USING AMYLOSUCRASE, AND SWEETENER USING THE TURANOSE

CROSS REFERENCE TO PRIOR APPLICATIONS

This application is a National Stage Patent Application of PCT International Patent Application No. PCT/KR2011/000645 (filed on Jan. 31, 2011) under 35 U.S.C. §371, which claims priority to Korean Patent Application No. 10-2010-0108174 (filed on Nov. 2, 2010), which are all hereby incorporated by reference in their entirety.

TECHNICAL FIELD

The present invention relates to a method of producing turanose using amylosucrase and a sweetener using the turanose.

BACKGROUND ART

Turanose is a reducing disaccharide naturally present in honey and its sweetness power is about half that of sucrose. It is an analog of sucrose, and has a chemical structure of 3-O-α-D-glucopyranosyl-D-fructose.

Because turanose is not fermented by a microorganism that causes dental caries, the turanose can be used as a calorie-free sweetener. Accordingly, turanose can play an important role in food, cosmetic, and pharmaceutic industries.

Japanese publications, patent No. 1993-252974 and J. Appl. Glycosci., 51, 223-227, are the only references that disclose an enzymatic process for producing turanose by treating an aqueous solution containing an amylaceous substance and fructose with cyclomaltodextrin glucanotransferase. In fact, the enzymatic process includes two important steps: transglycosylation of the amylaceous substances to fructose by cyclomaltodextrin glucanotransferase and hydrolyzation of the α-1,4-glucan chains of the transfer products by glucoamylase.

However, a method of easily producing high-purity and high-yield turanose has not been developed. Accordingly, it is very important to develop such a method of producing turanose so as to produce a calorie-free sweetener for use in foods, and additives for use in cosmetic products or medical products.

DISCLOSURE

Technical Problem

In response, the inventors of the present invention studied on how to produce high-purity turanose with high efficiency, and found that by acting amylosucrase as an zymogen on a substrate, such as sucrose, or the like, turanose was produced with high efficiency, and also, through a simple purification process, high-purity turanose was able to be produced with high-efficiency, thereby completing the present invention.

Accordingly, the present invention provides a method of producing high-yield and high-purity turanose in the industrial scale and a sweetener using the turanose.

According to an aspect of the present invention, a method of producing turanose includes acting amylosucrase on a sucrose solution to produce turanose, and purifying the reaction product.

Technical Solution

An aspect of the present invention provides a method of producing turanose according to an embodiment of the present invention, wherein the method includes acting amylosucrase on a sucrose solution to produce turanose, and purifying the reaction product.

Advantageous Effects

According to the present invention, the method of producing turanose using amylosucrase enables production of high-purity turanose through an enzymatic reaction occurring by treating a solution containing only sucrose or a solution containing fructose and sucrose with amylosucrase. Accordingly, turanose may be very useful for use as a calorie-free sweetener, and may function as a critical sweetener or additive in food, cosmetic, and pharmaceutic industries.

DESCRIPTION OF DRAWINGS

The above and other features and advantages of the present invention will become more apparent by describing in detail exemplary embodiments thereof with reference to the attached drawings in which.

BEST MODE

Figure 1:
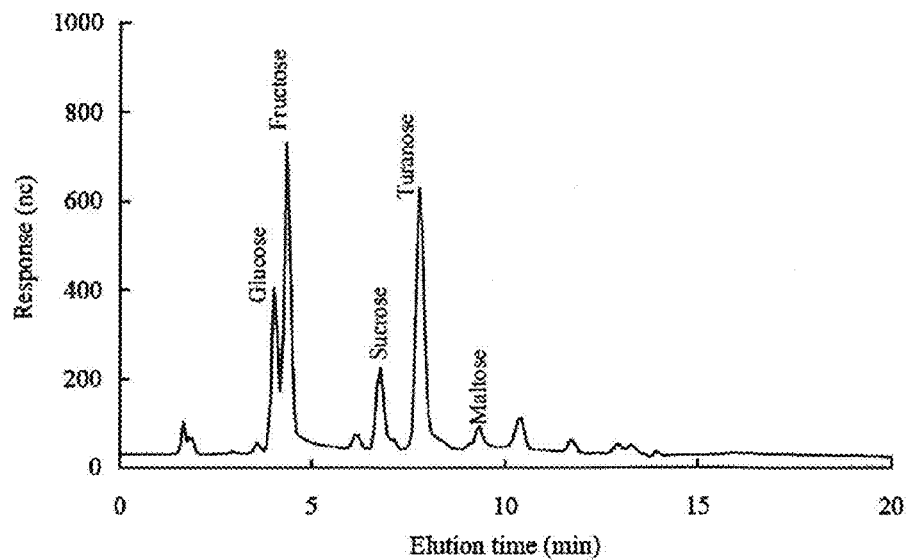
FIG. 1 shows a HPAEC chromatogram of a non-purified turanose sample.

An aspect of the present invention provides a method of producing turanose according to an embodiment of the present invention, wherein the method includes acting amylosucrase on a sucrose solution to produce a reaction product, and purifying the reaction product to obtain a turanose.

Amylosucrase used herein may be derived from any one of microorganism selected from the group consisting of microorganism *Neisseria polysaccharea*, *Deinococcus geothermalis*, and *Alteromonas macleodii*. For example, the amylosucrase may be derived from *Neisseria polysaccharea*, and may be isolated by using a method disclosed in U.S. Pat. No. 6,265,635.

According to an embodiment of the present invention, amylosucrase shows a maximum activity of 2.4 U/ml, and because an amount of turanose produced in this case is 2.38 mg/ml, it is confirmed that a specific activity of amylosucrase is 1.01 U/mg protein. Accordingly, in order to improve the yield of turanose, amylosucrase may be included in an amount of 20 to 500 mg, for example, 40 to 150 mg, based on 100 g of sucrose. If the amount of amylosucrase is outside this range, reaction conversion efficiency may be decreased or a side-reaction speed may be increased.

The microorganism *Neisseria polysaccharea* may be cultured in such a condition that a microorganism is grown to produce amylosucrase that constitutes an enzyme, and in general, the microorganism *Neisseria polysaccharea* may be isolated and cultured at a temperature of 37° C. and at a pH of 7.0 to 7.2. A culturing time may not be restricted as long as a microorganism is sufficiently grown, and for example, may be in a range of 24 to 48 hours. After the culturing of a microorganism is completed, cells may be collected from the culture through a typical solid liquid phase separation method. For example, centrifuging may be performed thereon at a temperature of 4° C. and then a supernatant thereof is removed to obtain cells.

In particular, an amylosucrase gene derived from the microorganism *Neisseria polysaccharea* may be expressed as a recombined proteinoplast in a host cell, for example, *E. coli*, bacillus, lactobacillus, or fungi.

As a cytozyme, a coenzyme extracted from a cell through a typical method may be used. For example, a coenzyme may be obtained as follows: an enzyme is extracted from a cell through a pulverization using ultrasonic waves or homogenation and then the extract is treated with centrifuging or membrane filtering. A coenzyme may be used without additional treatments or may be used after purification according to typical methods. For example, a coenzyme extract is filtered to remove insoluble materials therefrom, and the filtrate is passed through a nickel-nitrilotriacetic acid (Ni-NTA) affinity column to purify recombined $His_6$-tagged amylosucrase, and amicon ultra centrifugal filter devices are used at a temperature of 4° C. to elute the amylosucrase to obtain an electrophoretically uniform enzyme.

A purified enzyme may be directly used, or may be immobilized on a support material by using a typical method and then used. For example, a binding method with respect to an ion exchanger, a covalent binding or adsorption method with respect to a resin and a membrane may be used. Through this immobilization, an enzyme as a synthetic catalyst may be easily recollected and may be reused several times. In general, an enzyme purification process requires long process times and high costs. Accordingly, the immobilization and reuse of an enzyme may contribute to a substantial cost reduction.

An activity of purified amylosucrase according to the present invention may be measured by using the following method. That is, 100 μl of an enzyme solution is added to 900 μl of 50 mM Tris-HCl buffer solution (pH 7.0) including 0.1M sucrose as a substrate, and the mixture is reacted at a temperature of 35° C. for 30 minutes, and the reaction mixture is heated at a temperature of 100° C. for 10 minutes to stop the enzymatic reaction. An amount of fructose liberated into the reaction mixture is analyzed through a dinitrosalicylic acid (DNS) method using fructose as a reference material. One unit of amylosucrase activity is defined as an amount of enzyme that promotes production of 1 μmol fructose per minute under analysis conditions.

As a substrate used in the present invention, only sucrose may be used, or sucrose supplemented with fructose may be used. Concentrations of the used sucrose and fructose may not be particularly restricted. For example, even when acted on a 0.25M or 0.75M fructose-supplemented 1.0M or 2.5M sucrose solution which constitutes a substrate, the enzyme may act to produce turanose. Also, a solution including very high-concentration substrate or insoluble substrate may be used.

During the enzymatic reaction according to the present invention, a reaction temperature may not be limited as long as the enzyme is not deactivated. For example, the reaction temperature may be about 40° C. or less, or may be in a range of 20 to 40° C.

During the enzymatic reaction according to the present invention, a reaction pH may be in a range of about 6.0 to 9.0, for example, 6.5 to 7.5.

During the enzymatic reaction according to the present invention, the reaction time may vary according to an enzymatic reaction condition. For example, when 100-400 units/L of purified amylosucrase is used, the reaction time may be in a range of 24 to 120 hours.

In the reaction mixture obtained according to the present invention which is a saccharide composition, the yield of turanose may be 10% or more, for example, 50% or more, and for example, 73%. The obtained saccharide composition is filtered to remove impurities therefrom and then, decolorized with activated carbon.

Also, according to the production scale and reaction conditions, various high-purity purification methods may be used to purify and recollect the produced turanose. For example, ion-exchange resin chromatography, column chromatography using activated carbon, column chromatography using silicagel, fractional crystallization, or the like may be used to easily purify a product including high-purity turanose from the reaction mixture, and the obtained product is concentrated as a syrup product. If necessary, the syrup product is dried into a powder product.

Also, another aspect of the present invention provides a sweetener including a turanose that is produced by using the method described above.

Turanose is not fermented by a microorganism that causes dental caries. Accordingly, turanose may be very useful for use as a calorie-free sweetener, and may function as a critical sweetener or additive in food, cosmetic, and pharmaceutic industries.

MODE FOR INVENTION

Hereinafter, the present invention is described in detail with reference to examples below. However, the present invention is not limited to the examples.

Example 1

Enzyme Preparation and Purification

1. Preparation of Stock Culture of Recombinant *E. coli* BL21

A gene corresponding to NpAS was obtained from *Neisseria polysaccharea* ATCC 43768 through polymerized chain reaction (PCR) using 2 primers based on a *Neisseria polysaccharea* amylosucrase nucleotide sequence. That is, the PCR was carried out using *N. polysaccharea* genome DNA as a template and two oligonucleotides (SEQ ID NO:1: NPAS1 5'-GGA TCC GAT GTT GAC CCC CAC GCA GCA A-3'; and SEQ ID NO:2: NPAS2 5'-GGC AAG CTT CAG GCG ATT TCG AGC CAC AT-3').

The result PCR product was cloned in T-easy vector (Promega, Madison, Wis., USA), and any mistake that may occur during PCR was verified through DNA sequencing. An insert was cleaved by using BamHI and Hind III, and then the obtained fragment was inserted into a pRSET-B vector treated with the same enzyme to obtain pRSET-NpAS that constitutes NpAS expression vector. For the purpose of efficient gene expression, *E. coli* BL21 was transformed using the pRSET-NpAS.

2. Enzyme Preparation

A pH of a liquid nutrient culture medium including 1% (w/v) Bactotryptone, 0.5% (w/v) yeast extract, 0.5% (w/v) sodium chloride, and water was controlled to be 7.0. 500 ml of the culture medium was loaded into a 1000 ml Erlenmeyer flask that had been sterilized at a temperature of 120° C. for 15 minutes, followed by cooling, inoculation with the previously prepared stock culture of the recombined *E. coli* BL21, and incubation in the presence of 0.01% (w/v) ampicillin at a temperature of 37° C. When an optical density of cells was about 0.6, 1 ml of 0.1M isopropyl-β-D-thiogalactopyranoside was added to the culture to induce gene expression. After 12 hours of incubation at a temperature of 16° C., the culture was centrifuged at a temperature of 4° C. for 20 minutes at 5,500×g to harvest cells.

3. Enzyme Purification

The prepared culture was fully re-suspended with 50 ml of 50 mM Tris-HCl buffer solution (pH 7.0), and then cells were destroyed by using an ultrasonic pulverizing machine (Sonic Dismembrator 550, Fisher Scientific Co.) Model D100. The obtained mixture was centrifuged at a temperature of 4° C. for 20 minutes at 11,000×g to remove the cellular residue. The obtained supernatant was filtered through a 0.45 μm syringe filter, and then 5 ml of the filtrate was passed through a nickel-nitrilotriacetic acid (Ni-NTA) affinity column to purify the recombined $His_6$-tagged amylosucrase. Prior to elusion of the $His_6$-tagged amylosucrase, the Ni-NTA affinity column was washed with a 20 ml washing buffer solution (50 mM Tris, 300 mM sodium chloride, 20 mM imidazol, pH 7.0). Then, the amylosucrase protein was eluted with 5 ml of an elusion buffer solution (50 mM Tris, 300 mM sodium chloride, 250 mM imidazol, pH 7.0), followed by concentration using Amicon Ultra Centrifugal Filter Devices (Millipore Corporation, Billerica, USA) at a temperature of 4° C. As a result, an enzyme preparation having an electrophoretically single protein band was obtained.

Example 2

Non-Purified Turanose Preparation

1. Preparation of Turanose from Sucrose 400 units/L of the purified amylosucrase obtained as described above was added to a 2.0M sucrose-containing solution, and an enzymatic reaction was performed at a temperature of 35° C. for 72 hours. After the reaction, the enzyme was heated in boiled water for 10 minutes to be deactivated. The reaction product was assayed by using a DX-300 series HPAEC system (Dionex, USA) including a pulse current detector (Dionex, USA). In this case, the obtained saccharide was assayed using commercially available glucose, fructose, sucrose, maltose, and turanose as reference materials. Results thereof are shown in Table 1 and FIG. 1.

TABLE 1

| Saccharide | HPAEC retention time (min) | Saccharide composition (%) |
| --- | --- | --- |
| Glucose | 4.00 | 0.7 |
| Fructose | 4.33 | 20.7 |
| Sucrose | 6.75 | 4.9 |
| Turanose | 7.75 | 51.1 |
| Other saccharides | — | 22.6 |

2. Saccharide Composition Assay of Reaction Product According to Reaction Time 400 units/L of the purified amylosucrase obtained as described above was added to a 2.0M sucrose-containing solution, and an enzymatic reaction was performed at a temperature of 35° C. Samples were collected at predetermined time intervals, and the remaining enzyme was deactivated by heating at a temperature of 100° C. for 10 minutes. Thereafter, a saccharide composition of each of the samples was assayed using HPAEC in a manner similar to that used as described above, and results thereof are shown in Table 2.

TABLE 2

| Reaction time (hour) | Saccharide composition (%) | | | | |
| --- | --- | --- | --- | --- | --- |
| reaction time (hour) | Glucose | Fructose | Sucrose | Turanose | Other saccharides |
| 24 | 0.5 | 9.6 | 52.9 | 25.2 | 11.8 |
| 72 | 0.7 | 20.7 | 4.9 | 51.1 | 22.6 |
| 120 | 0.9 | 20.8 | 5.0 | 52.0 | 21.3 |

From table 2, it was confirmed that when the purified amylosucrase according to the present invention was acted on 2.0M sucrose as a substrate at a temperature of 35° C. for at least 72 hours, turanose occupied about 50% of the formed saccharide composition. Another major reaction product with the yield of about 20% was fructose, and glucose, non-consumed sucrose, and other saccharides constituted the rest of the composition.

Example 3

Effect of Enzyme Amount on Turanose Yield 100, 200, or 400 units/L of the purified amylosucrase according to the present invention was added to a 1.0M sucrose solution and the obtained mixture was enzymatically reacted at a temperature of 35° C. Samples were collected at predetermined time intervals, and the remaining enzyme was deactivated by heating at a temperature of 100° C. for 10 minutes. Thereafter, a saccharide composition of each of the samples was assayed using HPAEC, and turanose yields and reaction times of the respective samples at various enzymatic activity are shown in Table 3 below.

TABLE 3

| Turanose yield (%) | Enzyme amount (units/L) | | |
| --- | --- | --- | --- |
| turanose yield (%) | 100 | 200 | 400 |
| Reaction time (hour) 24 | 8.8 ± 0.3 | 19.3 ± 0.8 | 30.7 ± 0.2 |
| 72 | 27.4 ± 1.0 | 30.8 ± 0.2 | 31.7 ± 0.3 |
| 120 | 31.4 ± 0.5 | 31.6 ± 0.6 | 31.8 ± 0.5 |

From Table 3, it was confirmed that 100 units/L of purified amylosucrase resulted in the turanose yield of about 30% after 120 hours of reaction, and 400 units/L of purified amylosucrase resulted in the turanose yield of about 30% after only 24 hours of reaction.

Example 4

Effect of Temperature on Turanose Yield 400 units/L of the purified amylosucrase according to the present invention was added to a 1.0, 1.5, or 2.0M sucrose-containing solution, and an enzymatic reaction was performed at temperatures of 30, 35 and 40° C. After 72 hours of reaction, the sample was heated at a temperature of 100° C. for 10 minutes to deactivate the remaining enzyme, and a saccharide composition of each of the samples was assayed using HPAEC. Turanose yields of samples at various sucrose concentrations and temperatures are shown in Table 4 below.

TABLE 4

| Turanose yield (%) | | Temperature (° C.) | | |
|---|---|---|---|---|
| | | 30 | 35 | 40 |
| Sucrose concentration (M) | 1.0 | 33.9 ± 0.1 | 31.7 ± 0.3 | 29.6 ± 0.0 |
| sucrose concentration (M) | 1.5 | 38.7 ± 0.4 | 36.1 ± 0.5 | 34.7 ± 0.0 |
| sucrose concentration (M) | 2.0 | 34.2 ± 0.2 | 51.1 ± 0.0 | 38.7 ± 1.1 |

As shown in Table 4, when acted on 2.0M sucrose as a substrate at a temperature of 35° C. for 72 hours, the purified amylosucrase according to the present invention produced about 50% turanose.

Example 5

Effect of Sucrose Concentration on Turanose Yield 400 units/L of the purified amylosucrase according to the present invention was added to a 1.0, 1.5, 2.0 or 2.5M sucrose-containing solution, and the respective enzymatic reactions were performed at a temperature of 35° C. Samples were collected at predetermined time intervals, and the remaining enzyme was deactivated by heating at a temperature of 100° C. for 10 minutes. Thereafter, a saccharide composition of each of the samples was assayed using HPAEC, and turanose yields of the respective samples at various sucrose concentrations are shown in Table 5 below.

TABLE 5

| Turanose yield (%) | | Sucrose concentration (M) | | | |
|---|---|---|---|---|---|
| | | 1.0 | 1.5 | 2.0 | 2.5 |
| Reaction time (hour) | 24 | 30.7 ± 0.2 | 26.5 ± 0.2 | 25.1 ± 0.1 | 17.9 ± 0.0 |
| | 72 | 31.7 ± 0.3 | 36.1 ± 0.5 | 51.1 ± 0.0 | 41.0 ± 0.8 |
| | 120 | 31.8 ± 0.5 | 37.4 ± 0.3 | 52.0 ± 0.9 | 56.2 ± 0.3 |

As shown in Table 5, the higher the sucrose concentration is, the higher final concentration the turanose is. When 2.5M sucrose solution was used, after 120 hours of reaction, the enzyme produced turanose at a high yield of about 55%.

Example 6

Fructose Addition Effect on Turanose Yield

Solutions including various concentrations of sucrose (1.0, 1.5, or 2.0M) and fructose (0.25, 0.50, or 0.75M) were prepared, and then 400 units/L of the purified amylosucrase according to the present invention was added to the respective solutions, and an enzymatic reaction was performed thereon at a temperature of 35° C. After 96 hours of reaction, the samples were heated at a temperature of 100° C. for 10 minutes to deactivate the remaining enzyme, and saccharide compositions of the respective samples were assayed using HPAEC. Turanose yields of the respective samples at various sucrose and fructose concentrations are shown in Table 6 below.

TABLE 6

| Turanose yield (%) | | Fructose (M) | | | |
|---|---|---|---|---|---|
| turanose yield (%) | | 0 | 0.25 | 0.50 | 0.75 |
| Sucrose concentration (M) | 1.0 | 30.9 ± 0.8 | 45.8 ± 0.1 | 57.2 ± 0.2 | 62.8 ± 1.1 |
| sucrose concentration (M) | 1.5 | 36.5 ± 0.6 | 49.8 ± 0.1 | 58.6 ± 0.3 | 65.4 ± 0.4 |
| sucrose concentration (M) | 2.0 | 50.9 ± 0.1 | 60.0 ± 0.1 | 67.1 ± 0.4 | 73.1 ± 0.6 |

As shown in Table 6, the higher the fructose concentration is, finally, more turanose was produced. When 0.75M fructose was added to the respective reaction media, the enzyme produced turanose with a high yield of about 60%.

Example 7

Preparation of Purified Turanose from Sucrose

1. Enzyme Preparation and Purification

A stock culture of recombined *E. coli* BL21 was inoculated on 5 L of sterilized liquid nutrient culture medium including 1% (w/v) Bactotryptone, 0.5% (w/v) yeast extract, 0.5% (w/v) sodium chloride, and water, followed by incubation in the presence of 0.01% (w/v) ampicillin at a temperature of 37° C. for 4 hours. Thereafter, 10 ml of 0.1M isopropyl-β-D-thiogalactopyranoside was added to the culture. After 16 hours of incubation at a temperature of 16° C., centrifuging was performed thereon at a temperature of 4° C. for 30 minutes at 5,500×g to harvest cells.

The obtained cell culture was re-suspended with 500 ml of 50 mM Tris-HCl buffer solution (pH 7.0), and then, cells were destroyed by using an ultrasonic pulverizing machine (Sonic Dismembrator 550, Fisher Scientific Co.) Model D100. The obtained cell suspension was centrifuged to obtain a supernatant, and the supernatant was filtered through a 0.45 μm syringe filter, purified through a nickel-nitrilotriacetic acid (Ni-NTA) affinity column, and concentrated by using an amicon ultra centrifugal filter devices (Millipore Corporation, Billerica, USA). About 100 ml of concentrated enzyme solution showed, finally, an activity of about 2.4 units/ml.

2. Preparation of Purified Turanose from Sucrose

A solution including sucrose having a final concentration of 2.5M was prepared, and 400 units/L of the purified amylosucrase was added to the solution, and then an enzymatic reaction was performed thereon at a temperature of 35° C. for 120 hours. Thereafter, the reaction mixture was heated at a temperature of 100° C. for 10 minutes, cooled, filtered through a 0.45 μm syringe filter to remove insoluble materials therefrom, and purified by preparative high-speed liquid chromatography (model LC-9104; JAI Ltd., Tokyo, Japan) sequentially including two hydrophilic preparative columns of JAIGEL W-251 and W-252 (20 mm×500 mm). Samples were eluted with deionized water at a flow rate of 3 mL/min. A turanose fraction was obtained, concentrated, and lyophilized to produce turanose-rich saccharide powder with a purity of about 96% and a yield of about 65%.

3. Sugar Composition Assay

Sugar composition assay was performed on the high-purity saccharide powder including turanose.

1) HPAEC

Figure 3:
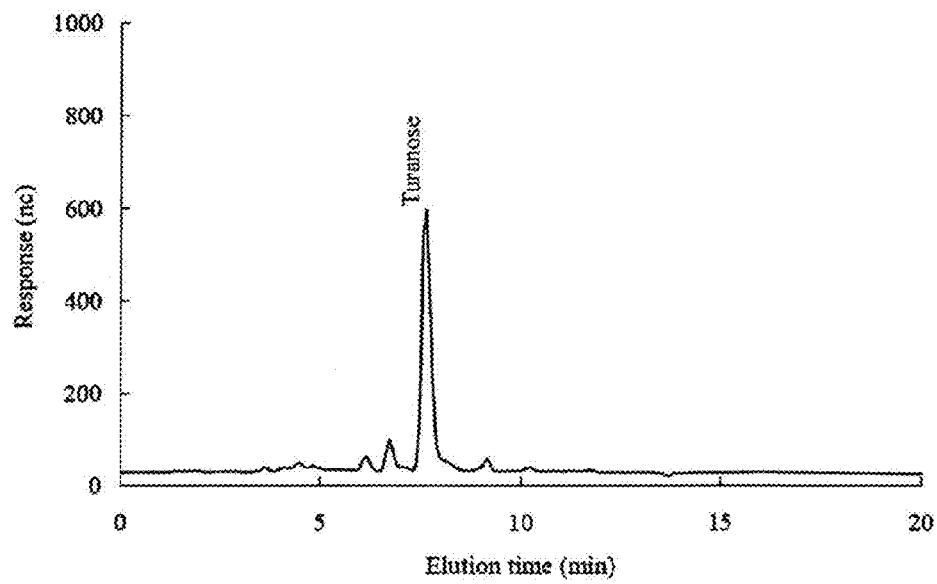
FIG. 3 shows a HPAEC chromatogram of a purified turanose sample.

The high-purity saccharide powder was assayed by using a DX-300 series HPAEC system (Dionex, USA) including a pulse current detector (Dionex, USA), and in this case, commercially available glucose, fructose, sucrose, maltose and turanose were used as reference materials. As a result, as shown in FIG. 3, it was confirmed that turanose was formed from sucrose.

2) HPLC-MS

The mass spectrum of the purified turanose was obtained on Agilent 1100 series MSD (Agilent Technologies, Palo Alto, Calif., USA) by using a cation electrospray mode. The sample solution was delivered at a flow rate of 0.8 ml/min to an electrosprayer and a loading amount was 10 μl. While a capillary voltage was maintained at 4 kV, a fragmentor voltage was fixed at 150 V. The temperature of the electrosprayer was maintained at 350° C., and a detection scan range was in a range of m/z 100 to 1400.

Figure 4:
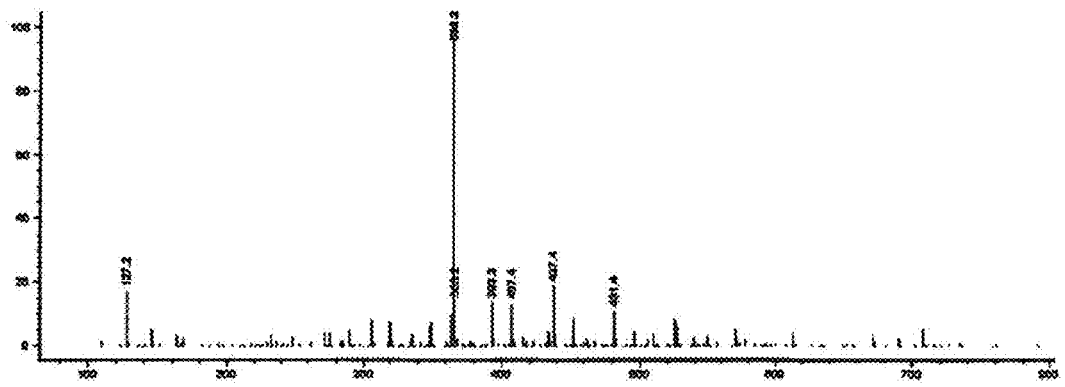

As a result, as shown in FIG. 4, the high-purity saccharide powder showed a peak corresponding to an ion $(M+Na)^+$ at MS m/z 365.3 and thus, it was confirmed that the saccharide was disaccharide.

3) NMR

NMR assay was performed using a 600 MHz NMR system (Rheinstetten, Germany), and in this case, the purified turanose was used as being dissolved in pure water $D_2O$. A heteronuclear single quantum correlation (HSQC), $^{13}C$ and $^1H$ NMR spectra thereof were recoded according to a standard experimental method. Data process was performed using TopSpin® 2.0 software (Bruker BioSpin, Rheinstetten, Germany).

Figure 5:
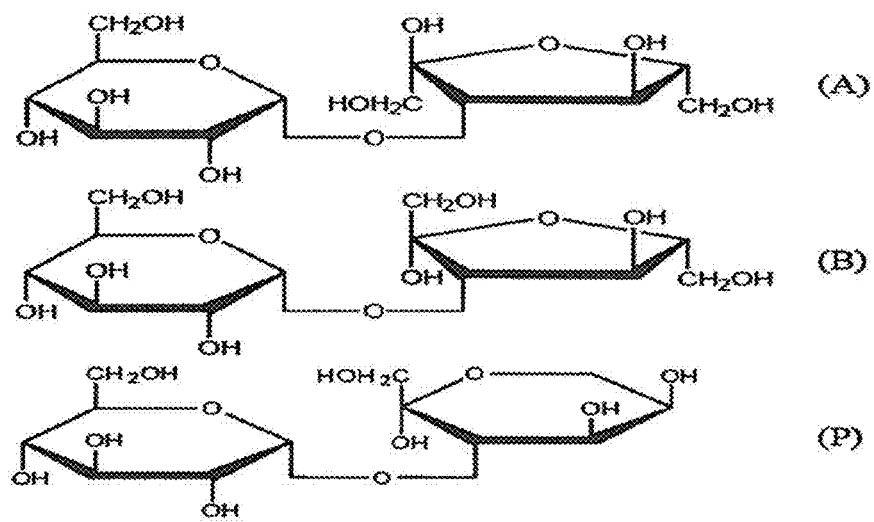
FIG. 5 shows the purified turanoses analyzed based on NMR spectrum.

The purified turanose was analyzed based on $^{13}C$ NMR spectrum thereof, and as shown in Table 7 below and FIG. 5, it was confirmed that the purified turanose was a turanose tautomer, such as 3-O-α-D-glucopyranosyl-α-D-fructofuranose, 3-O-α-D-glucopyranosyl-β-D-fructofuranose, or 3-O-α-D-glucopyranosyl-β-D-fructopyranose.

Example 8

Preparation of Purified Turanose from Sucrose

Figure 2:
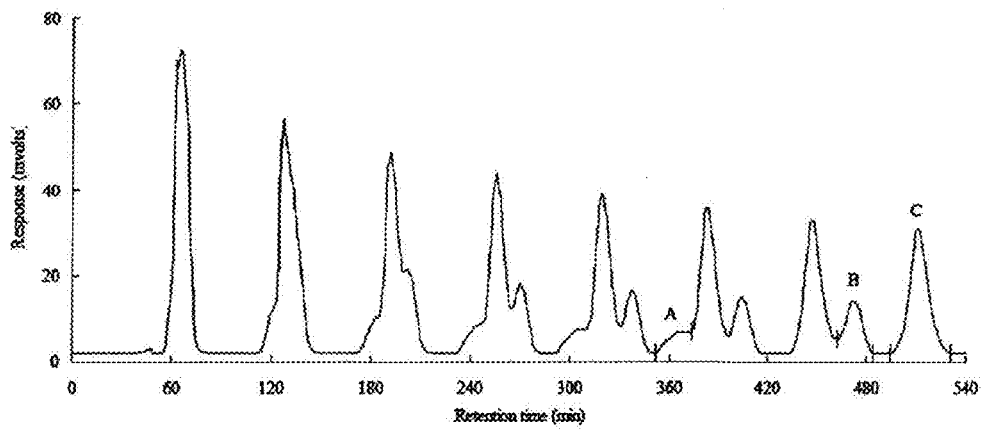
FIGS. 2 and 4 show a HPLC-MS chromatogram of a purified turanose sample respectively.

A solution including sucrose with a final concentration of 2.0M and fructose with a final concentration of 0.75M was prepared, and 400 units/L of the purified amylosucrase was added to the solution, and an enzymatic reaction was performed at a temperature of 35° C. for 96 hours. Thereafter, the reaction mixture was heated at a temperature of 100° C. for 10 minutes to deactivate the remaining enzyme, followed by cooling to room temperature. The obtained reaction mixture included about 73% of turanose (see FIG. 1). To isolate turanose from other components, the reaction mixture was filtered through a 0.45 μm syringe filter to remove insoluble materials therefrom, and then subjected to a preparative high-speed liquid chromatography (model LC-9104; JAI Ltd., Tokyo, Japan) sequentially including two hydrophilic preparative columns of JAIGEL W-251 and W-252 (20 mm×500 mm). Samples were eluted with deionized water at a flow rate of 3 mUmin. A turanose fraction (fraction C of FIG. 2) were obtained, concentrated, and lyophilized to produce turanose-rich saccharide powder with a purity of about 96% and a yield of about 65.

According the present invention, a solution that includes only sucrose or a solution that includes fructose and sucrose is treated with amylosucrase so that high-purity turanose is easily produced and isolated from a substrate, such as sucrose, and the produced turanose has a high degree of purity. Accordingly, the turanose may be useful for use as a critical calorie-free sweetener or additive in food, cosmetic, and pharmaceutic industries.

TABLE 7

| Tautomer<br>호변이체<br>호변이체 | Chemical shift (ppm) | | | | | | | | | | | |
|---|---|---|---|---|---|---|---|---|---|---|---|---|
| | α-D-glucopyranosyl unit | | | | | | D-fructose unit | | | | | |
| | C-1 | C-2 | C-3 | C-4 | C-5 | C-6 | C-1 | C-2 | C-3 | C-4 | C-5 | C-6 |
| 3-O-α-D-glucopyranosyl-α-D-fructofuranose | 97.1 | 71.5 | 73.1 | 69.6 | 74.8 | 60.5 | 61.3 | 104.5 | 85.0 | 72.5 | 81.8 | 63.0 |
| 3-O-α-D-glucopyranosyl-β-D-fructofuranose | 98.7 | 71.7 | 72.9 | 69.6 | 74.6 | 60.5 | 62.5 | 101.9 | 80.8 | 72.6 | 81.1 | 63.1 |
| 3-O-α-D-glucopyranosyl-β-D-fructopyranos | 101.2 | 72.3 | 73.1 | 69.6 | 73.0 | 60.7 | 64.3 | 98.0 | 76.9 | 70.5 | 69.3 | 63.6 |

4) TLC

TLC assay was carried out by using a Whatman K6 silica-gel plate, and in this case, acetonitrile, ethylacetate, 1-propanol, and water (85:20:20:15 v/v) were used as a solvent system. 0.3% (w/v) N-(1-naphthyl)-ethylenediamine and 5% (v/v) sulfuric acid dissolved in methanol were sprayed into the plate and then the plate was heated at a temperature of 110° C. for 10 minutes to colorize the plate.

Figure 6:
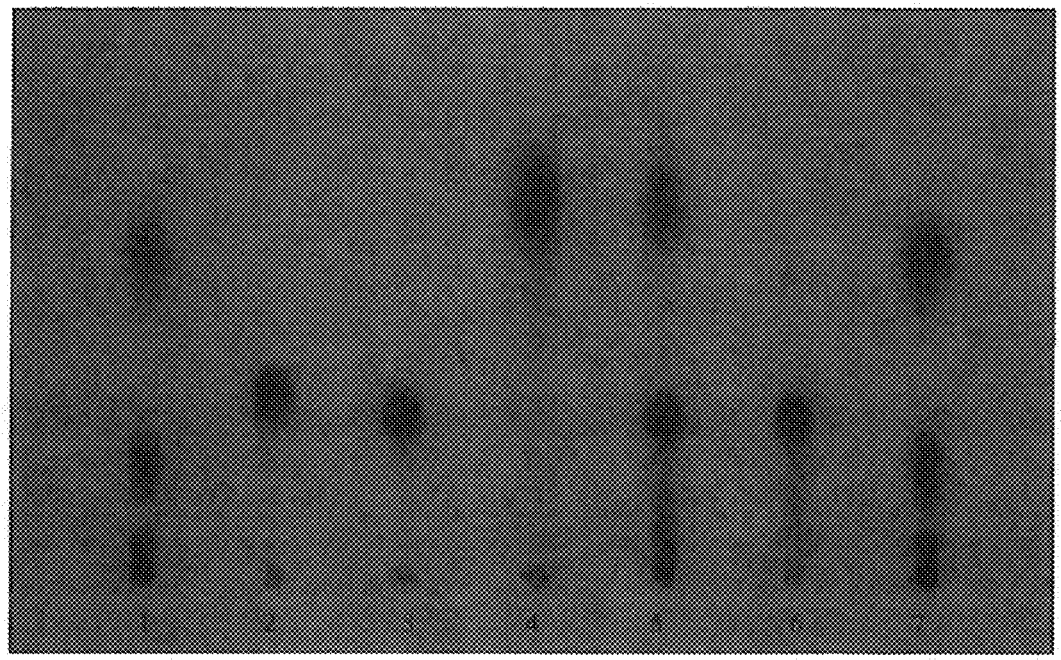
FIG. 6 shows a TLC chromatogram of a purified turanose sample, wherein Lanes 1 and 7 show results of G1(glucose)-G7 (maltoheptaose) reference material; Lane 2 shows results of a sucrose reference material; Lane 3 shows results of a turanose reference material; Lane 4 shows results of a fructose reference material; Lane 5 shows results of a non-purified turanose sample; and Lane 6 shows results of a purified turanose sample.

As a result, as illustrated in FIG. 6, it was confirmed that the saccharide was turanose.

It should be understood that the exemplary embodiments described herein should be considered in a descriptive sense only and not for purposes of limitation. Descriptions of features or aspects within each embodiment should typically be considered as available for other similar features or aspects in other embodiments.

Sequence List Text

SEQ ID NO: 1 is a sequence of NPAS1 primer, and

SEQ ID NO 2 is a sequence of NPAS2 primer.

What is claimed is:

1. A method of producing turanose, the method comprising: adding an amylosucrase to a mixed solution having a sucrose and a fructose to produce a reaction product, and purifying the reaction product to obtain a turanose, wherein a concentration of the sucrose contained in the mixed solution is in a range of 1.0 to 2.5M and a concentration of the fructose contained in the mixed solution is in a range of 0.25 to 0.75M.

2. The method of claim 1, wherein the amylosucrase is derived from a microorganism selected from the group consisting of *Neisseria polysaccharea*, *Deinococcus geothermalis*, and *Alteromonas macleodii*.

3. The method of claim 1, wherein a reaction temperature is in a range of 30 to 40° C.

4. The method of claim 1, wherein a reaction pH is in a range of 6.5 to 7.5.

5. The method of claim 1, wherein when 100-400 units/L of the amylosucrase is added, a reaction time is in a range of 24 to 120 hours.

6. The method of claim 1, wherein the purifying step is performed by a process selected from the group consisting of ion-exchange resin chromatography, column chromatography using activated carbon, and column chromatography using silica gel.

* * * * *